(12) United States Patent
Wu

(10) Patent No.: US 12,187,704 B2
(45) Date of Patent: *Jan. 7, 2025

(54) TRIAZINE DERIVATIVES AND METHODS OF USE THEREOF

(71) Applicant: Ascletis BioScience Co., Ltd., Hangzhou (CN)

(72) Inventor: Jinzi Jason Wu, Hangzhou (CN)

(73) Assignee: Ascletis BioScience Co., Ltd., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,502

(22) Filed: May 30, 2023

(65) Prior Publication Data

US 2024/0182448 A1    Jun. 6, 2024

Related U.S. Application Data

(63) Continuation of application No. 18/064,419, filed on Dec. 12, 2022, now Pat. No. 11,702,406.

(30) Foreign Application Priority Data

Nov. 21, 2022   (CN) .......................... 202211453696.4

(51) Int. Cl.
  *C07D 401/14*      (2006.01)
  *C07D 403/14*      (2006.01)

(52) U.S. Cl.
  CPC ......... *C07D 401/14* (2013.01); *C07D 403/14* (2013.01); *C07B 2200/05* (2013.01)

(58) Field of Classification Search
  CPC .. C07D 401/14; C07D 403/14; C07B 2200/05
  USPC ........................................................ 514/245
  See application file for complete search history.

(56) References Cited

U.S. PATENT DOCUMENTS

| | | | |
|---|---|---|---|
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 2021/0292283 A1 | 9/2021 | Tanaka et al. | |

FOREIGN PATENT DOCUMENTS

| | | | |
|---|---|---|---|
| WO | 2010092966 | 8/2010 | |
| WO | 2013089212 | 6/2013 | |
| WO | 2012020749 | 2/2021 | |
| WO | WO-2022138987 A1 * | 6/2022 | |

OTHER PUBLICATIONS

U.S. Appl. No. 18/064,419, filed Dec. 12, 2022, Patented.
Berge et al. "Pharmaceutical Salts" Journal of Pharmaceutical Sciences, 1977, vol. 66, pp. 1-19.

* cited by examiner

*Primary Examiner* — Kahsay Habte
(74) *Attorney, Agent, or Firm* — Samson G. Yu

(57) ABSTRACT

Certain antiviral compounds, pharmaceutical compositions, and methods related thereto are disclosed.

11 Claims, No Drawings

TRIAZINE DERIVATIVES AND METHODS OF USE THEREOF

This application is a Continuation Application of U.S. patent application Ser. No. 18/064,419, which was filed on Dec. 12, 2022, which claims priority of Chinese patent application no. CN202211453696.4, filed on Nov. 21, 2022, which is incorporated herein by reference in its entirety.

FIELD

This application generally relates to Triazine derivatives, as well as compositions and methods of use related thereto.

BACKGROUND

Coronaviruses (CoV) are a family of enveloped positive-stranded RNA pathogenic viruses that can cause acute and chronic diseases, including central nervous system disorders, the common cold, lower respiratory tract infections, and diarrhea. HcoV-229E and HcoV-OC43 are the first zoonotic strains to be identified since 1995. In 2003, the severe acute respiratory syndrome coronavirus, now named SARS-COV-1, caused the first global human coronavirus pandemic, resulting in more than 8,000 progressive respiratory failures and 916 deaths (10 to 15% mortality). Over the next eight years, significantly less lethal zoonotic coronaviruses HcoV-NL64 and HcoV-HKU1, were identified. In 2012, the SARs-like Middle East respiratory syndrome coronavirus (MERS-COV) was discovered, which has a low rate of transmission but a high mortality rate, From 2012 to Feb. 2, 2021, there were 2567 confirmed infections and 882 deaths worldwide (34% mortality) from its emergence. In 2020, SARS-COV-2 pneumonia (COVID-19) caused by severe acute respiratory syndrome coronavirus-2 (SARS-COV-2) is now spreading globally and has become a worldwide epidemic, posing a serious challenge to global public health defense and healthcare systems and creating uncertainty for the world economy.

3Clpro is a potentially target for the development of drugs against broad-spectrum coronaviruses. Currently reported 3Clpro inhibitors have poor target selectivity, unpredictable toxic side effects, poor metabolic stability, weak enzyme inhibition activity, and poor drug performance. Therefore, there still exist a need for more effective 3Clpro inhibitors.

SUMMARY

One aspect of the present application relates to compounds having a structure as shown in Formula I:

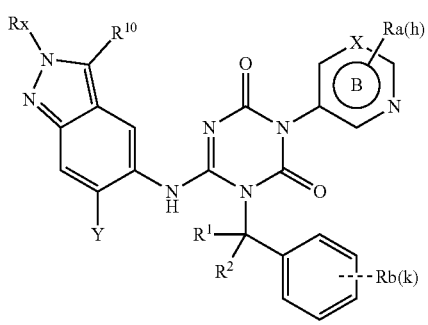

pharmaceutically acceptable salts, deuterium substitutes, isomers, prodrugs, and metabolites thereof;

wherein $R^1$, $R^2$ or $R^{10}$ is independently selected from hydrogen, halogen, and deuterium;

Rx is selected from hydrogen, deuterium, cyano, alkyl, alkenyl, and alkynyl; wherein the alkyl, alkenyl, or alkynyl is optionally substituted with 1 to 3 substituents each independently selected from deuterium, halogen, hydroxyl, cyano, and alkoxy;

Rb is selected from hydrogen, deuterium, halogen, and cyano;

k=2, 3 or 4;

B ring is a six-membered heteroaromatic ring containing N and is substituted with h number of Ra;

Ra is selected from hydrogen, deuterium, halogen, haloalkyl and alkyl;

h=0, 1 or 2;

X is C or N; and

Y is selected from alkyl, Cl and Br.

Another aspect of the present application relates to a compound having a structure selected from the group consisting of

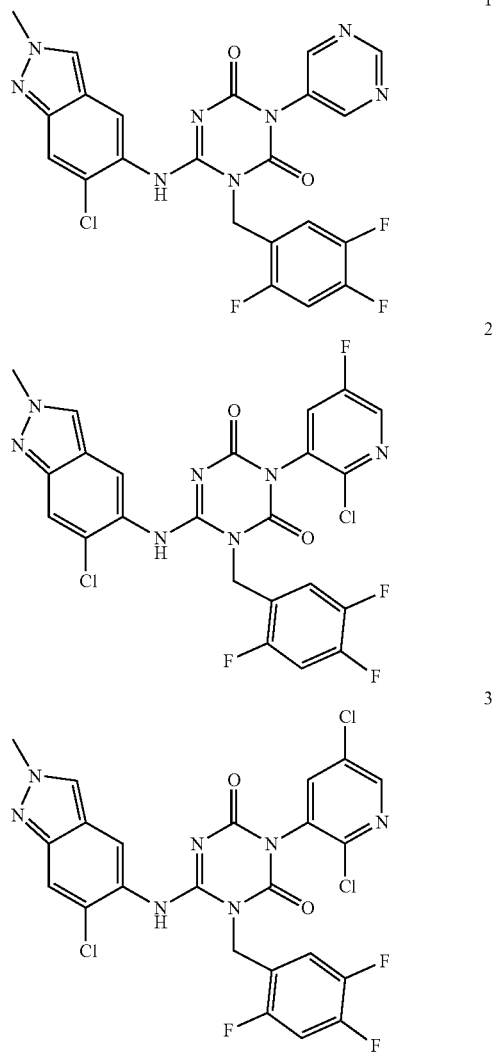

-continued

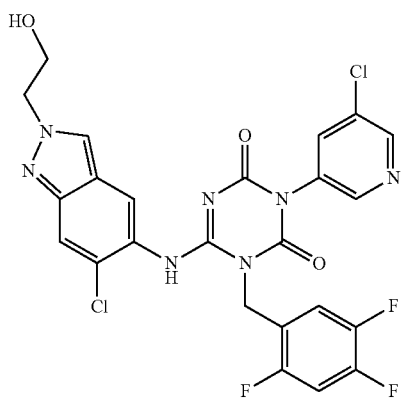
4

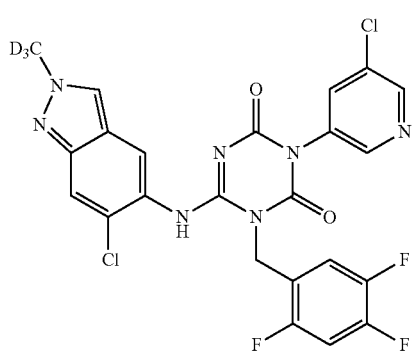
5

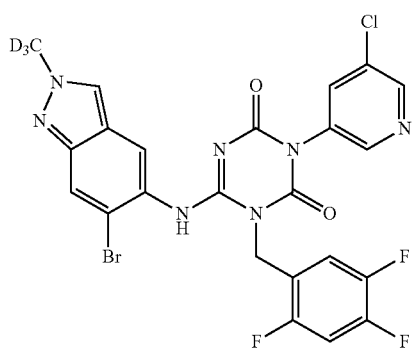
6

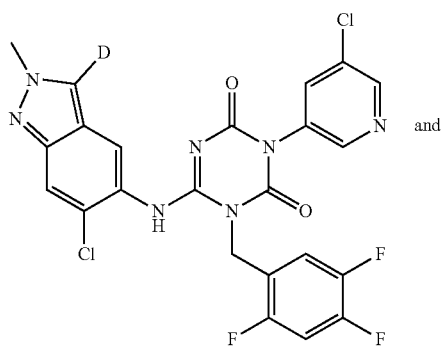
7 and

-continued

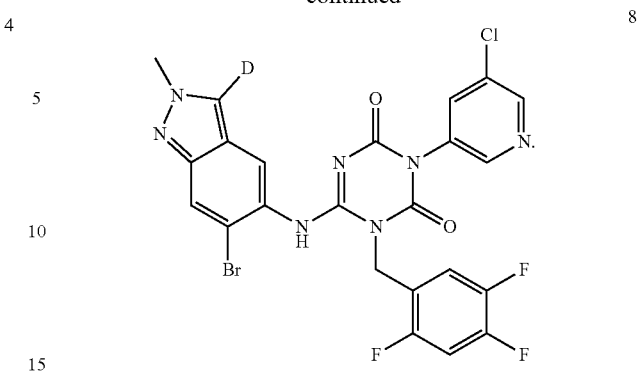
8

DETAILED DESCRIPTION

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug At various places in the present specification, certain features of the compounds are disclosed in groups or in ranges. It is specifically intended that such a disclosure includes each and every individual subcombination of the members of such groups and ranges.

The compounds described herein can be asymmetric (e.g, having one or more stereocenters). All stereoisomers, such as enantiomers and diastereomers, are intended unless otherwise indicated. Compounds of the present application that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present application. Cis and trans geometric isomers of the compounds of the present application are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as b-camphorsulfonic acid. Other resolving agents suitable for fractional crystallization methods include stereoisomerically pure forms of a-methylbenzylamine (e.g., S and R forms, or diastereomerically pure forms), 2-phenylglycinol, norephedrine, ephedrine, TV-methyl-ephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In compounds with more than one chiral centers, each of the chiral centers in the compound may be independently (R) or (S), unless otherwise indicated.

Compounds of the application also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine -imine pairs, and annular forms where a proton can occupy two or more positions of a heterocyclic system, e.g., 1H- and 3/f-imidazole, 1H-, 2H- and 4H-1,2,4-triazole, \H- and 211-isoindole and 1H- and 2//-pyrazole. Tautomeric forms can be in equilibrium or sterically locked into one form by appropriate substitution.

Compounds of the application can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the application can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms.

I. Definitions

The term, "compound," as used herein is meant to include all stereoisomers, geometric isomers, tautomers and isotopes of the structures depicted. The term is also meant to refer to compounds of the applications, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the application, or salts thereof, are substantially isolated. By "substantially isolated" is meant that the compound is at least partially or substantially separated from the environment in which it was formed or detected. Partial separation can include, e.g., a composition enriched in the compounds of the application. Substantial separation can include compositions containing at least about 50%, at least about 60%, at least about 70%, at least about 80%, at least about 90%, at least about 95%, at least about 97%, or at least about 99% by weight of the compounds of the application, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present application also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the non-toxic salts of the parent compound formed, e.g., from non toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, non-aqueous media like ether, ethyl acetate, alcohols (e.g., methanol, ethanol, iso-propanol or butanol) or acetonitrile (MeCN) are preferred. Lists of suitable salts are found in Remington's Pharmaceutical Sciences, 17th Ed., (Mack Publishing Company, Easton, 1985), p. 1418, Berge et al., J. Pharm. Sci, 1977, 66(1), 1-19 and in Stahl et al., Handbook of Pharmaceutical Salts: Properties, Selection, and Use, (Wiley, 2002). In some embodiments, the compounds described herein include the N-oxide forms.

The terms "subject," "individual," and "patient," are used interchangeably and refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

The term "solvate" refers to the compound formed by the interaction of a solvent and an effective pharmaceutical ingredient, a metabolite, or salt thereof. Suitable solvates are pharmaceutically acceptable solvates including hydrates The term "substituted" or "optionally substituted" as used in the present invention means that one or more hydrogen atoms of the group to which the term "substitute" or "optionally substituted" refers are replaced with one or more substituents. In some embodiments, each of the one or more substitutents is independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower arylalkyloxyalkyl, provided that the normal valency of the atom on which the substitution is considered is not exceeded and that the substitution results in a stable chemical compound, that is to say a compound that is sufficiently robust to be isolated from a reaction mixture.

The term "alkyl" refers to a straight or branched or cyclic chain hydrocarbon radical with only single carbon-carbon bonds. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted.

The term "aryl" refers to aromatic groups which have 5-14 ring atoms and at least one ring having a conjugated pi electron system and includes carbocyclic aryl, heterocyclic aryl and biaryl groups, all of which may be optionally substituted.

Carbocyclic aryl groups are groups which have 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups which have 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl.

The term "substituted aryl" and "substituted heteroaryl" refers to aryl and heteroaryl groups substituted with 1-3 substituents. In some embodiments, the 1-3 substituents are each independently selected from the group consisting of lower alkyl, lower alkoxy, lower perhaloalkyl, halo, hydroxy, and amino.

The term "-aralkyl" refers to an alkylene group substituted with an aryl group Suitable aralkyl groups include benzyl, picolyl, and the like, and may be optionally substituted.

The term "heteroarylalkyl" refers to an alkylene group substituted with a heteroaryl group.

The term "alkylaryl-" refers to an aryl group substituted with an alkyl group. "Lower alkylaryl-" refers to such groups where alkyl is lower alkyl.

As used herein, the carbon atom designations may have the indicated integer and any intervening integer. For example, the number of carbon atoms in a $(C_1-C_4)$-alkyl group is 1, 2, 3, or 4. It should be understood that these designations refer to the total number of atoms in the corresponding hetero group, including carbon atoms and heteroatoms. For example, in a $(C_3-C_{10})$-heterocyclyl the total number of carbon atoms and heteroatoms is 3 (as in aziridine), 4, 5, 6 (as in morpholine), 7, 8, 9, or 10.

The term "lower" referred to herein in connection with organic radicals or compounds respectively refers to 6 carbon atoms or less. Such groups may be straight chain, branched, or cyclic.

The term "higher" referred to herein in connection with organic radicals or compounds respectively refers to 7 or more carbon atoms. Such groups may be straight chain, branched, or cyclic.

The term "cyclic alkyl" or "cycloalkyl" refers to alkyl groups that are cyclic of 3 to 10 carbon atoms, and in one aspect are 3 to 6 carbon atoms. Suitable cyclic groups include fused cyclic group, spiro cyclic group, norbornyl and cyclopropyl. Such groups may be substituted.

The term "heterocyclic," "heterocyclic alkyl" or "heterocycloalkyl" refer to cyclic groups of 3 to 10 atoms, and in one aspect cyclic groups of 3 to 6 atoms, that contain at least one heteroatom, in a further aspect 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spiro-cyclic groups. Suitable heterocyclic groups include pyrrolidinyl, morpholino, morpholinoethyl, and pyridyl.

The terms "arylamino" (a), and "aralkylamino" (b), respectively, refer to the group —NRR', wherein respectively, (a) R is aryl and R' is hydrogen, alkyl, aralkyl, heterocycloalkyl, or aryl, and (b) R is aralkyl and R' is hydrogen, aralkyl, aryl, alkyl or heterocycloalkyl.

The term "acyl" refers to —C(O)—R, where R is alkyl, heterocycloalkyl, or aryl.

The term "carboxy esters" refers to —C(O)—OR, where R is alkyl, aryl, aralkyl, cyclic alkyl, or beterocycloalkyl, all optionally substituted.

The term "carboxyl" refers to —C(O)—OH.

The term "oxo" refers to =O in an alkyl or heterocycloalkyl group.

The term "amino" refers to —NRR', where R and R' are independently selected from hydrogen, alkyl, aryl, aralkyl and heterocycloalkyl, all except H are optionally substituted; and R and R' can form a cyclic ring system.

The term "-carboxylamido" refers to —C(O)NR$_2$, where each R is independently hydrogen or alkyl.

The term "-sulphonylamido" or "-sulfonylamido" refers to —S(=O)$_2$NR$_2$ where each R is independently hydrogen or alkyl.

The term "halogen" or"halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "sulphonyl" or "sulfonyl" refers to —SO$_2$R, where R is H, alkyl, aryl, aralkyl, or heterocycloalkyl.

The term "sulphonate" or "sulfonate" refers to —SO$_2$—OR, where R is —H, alkyl, aryl, aralkyl, or heterocycloalkyl.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl The term "1-Alkenyl" refers to alkenyl groups where the double bond is between the first and second carbon atom. If the 1-alkenyl group is attached to another group, e.g., it is a W substituent attached to the cyclic phosphonate, it is attached at the first carbon.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-Alkynyl" refers to alkynyl groups where the triple bond is between the first and second carbon atom. If the 1-alkynyl group is attached to another group, e g., it is a W substituent attached to the cyclic phosphonate, it is attached at the first carbon.

The term "alkylene" refers to a divalent straight chain, branched chain or cyclic saturated aliphatic group. In one aspect the alkylene group contains up to and including 10 atoms. In another aspect the alkylene group contains up to and including 6 atoms. In a further aspect the alkylene group contains up to and including 4 atoms. The alkylene group can be either straight, branched or cyclic The term "acyloxy" refers to the ester group —O—C(O)R, where R is H, alkyl, alkenyl, alkynyl, aryl, aralkyl, or heterocycloalkyl.

The term "aminoalkyl-" refers to the group NR$^2$-alk- wherein"alk" is an alkylene group and R is selected from —H, alkyl, aryl, aralkyl, and heterocycloalkyl.

The term "alkylaminoalkyl-" refers to the group alkyl-NR-alk- wherein each"alk" is an independently selected alkylene, and R is H or lower alkyl. "Lower alkylaminoalkyl-" refers to groups where the alkyl and the alkylene group is lower alkyl and alkylene, respectively.

The term "arylaminoalkyl-" refers to the group aryl-NR-alk- wherein "alk" is an alkylene group and R is —H, alkyl, aryl, aralkyl, or heterocycloalkyl. In "lower arylaminoalkyl-," the alkylene group is lower alkylene.

The term "alkylaminoaryl-" refers to the group alkyl-NR-aryl- wherein "aryl" is a divalent group and R is —H, alkyl, aralkyl, or heterocycloalkyl. In "lower alkylaminoaryl-," the alkyl group is lower alkyl.

The term "alkoxyaryl-" refers to an aryl group substituted with an alkyloxy group In "lower alkyloxyaryl-," the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or"alkyloxy-" refers to the group alkyl-O—.

The term "alkoxyalkyl-" or "alkyloxyalkyl-" refers to the group alkyl-O-alk- wherein"alk" is an alkylene group. In "lower alkoxyalkyl-," each alkyl and alkylene is lower alkyl and alkylene, respectively.

The term "alkylthio-" refers to the group alkyl-S—.

The term "alkylthioalkyl-" refers to the group alkyl-S-alk- wherein"alk" is an alkylene group. In "lower alkylthioalkyl-," each alkyl and alkylene is lower alkyl and alkylene, respectively.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "amido" refers to the NR$_2$ group next to an acyl or sulfonyl group as in NR$_2$—C(O)—, RC(O)—NR$^1$—, NR$_2$—S(=O)$_2$— and RS(=O)$_1$—, where R and R$^1$ include —H, alkyl, aryl, aralkyl, and heterocycloalkyl.

The term "carboxamido" refer to NR$^2$—C(O)— and RC(O)—NR$^1$—, where R and R$^1$ include —H, alkyl, aryl, aralkyl, and heterocycloalkyl. The term does not include urea, —NR—C(O)—NR—.

The term "sulphonamido" or "sulfonamido" refer to NR$_2$—S(=O)$_2$— and RS(=O)$_2$—NR$^1$—, where R and R$^1$ include —H, alkyl, aryl, aralkyl, and heterocycloalkyl. The term does not include sulfonylurea, —NR—S(=O)$_2$—NR—.

The term "carboxamidoalkylaryl" or "carboxamidoaryl" refers to an aryl-alk-NR$^1$—C(O), and aryl-NR$^1$—C(O)-alk-, respectively, where "alk" is alkylene, R$^1$ and R include H, alkyl, aryl, aralkyl, and heterocycloalkyl.

The term "sulfonamidoalkylaryl" or "sulfonamidoaryl" refers to an aryl-alk-NR$^1$-S(=O)$_2$—, and aryl-NR$^1$—S(=O)$_2$—, respectively, where "alk" is alkylene, R$^1$ and R include —H, alkyl, aryl, aralkyl, and heterocycloalkyl.

The term "hydroxyalkyl" refers to an alkyl group substituted with one —OH.

The term "haloalkyl" refers to an alkyl group substituted with halo. The term "cyano" refers to —CN.

The term "nitro" refers to —NO$_2$.

The term "acylalkyl" refers to an alkyl-C(O)-alk-, where-"alk" is alkylene.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups, wherein "alk" is lower alkylen.

The term "heteroarylalkyl" refers to an alkylene group substituted with a heteroaryl group.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the term "combination with" when used to describe administration with an additional treatment means that the agent can be administered prior to, together with, or after the additional treatment, or a combination thereof.

II. Compounds and Compositions of the Present Application

One aspect of the present application relates to compounds having a structure as shown in Formula I:

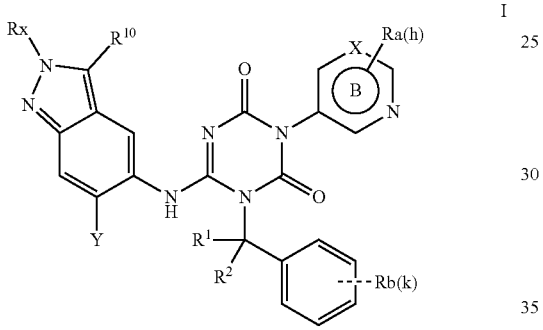

pharmaceutically acceptable salts, deuterium substitutes, isomers, prodrugs, and metabolites thereof;
wherein
$R^1$, $R^2$ or $R^{10}$ is independently selected from hydrogen, halogen, and deuterium;
Rx is selected from hydrogen, deuterium, cyano, alkyl, alkenyl, and alkynyl; wherein the alkyl, alkenyl, or alkynyl is optionally substituted with 1 to 3 substituents each independently selected from deuterium, halogen, hydroxyl, cyano, and alkoxy;
Rb is selected from hydrogen, deuterium, halogen, and cyano;
k=2, 3 or 4;
B ring is a six-membered heteroaromatic ring containing N and is substituted with h number of Ra;
Ra is selected from hydrogen, deuterium, halogen, haloalkyl and alkyl;
h=0, 1 or 2;
X is C or N; and
Y is selected from alkyl, Cl and Br.

In some embodiments, Rx is selected from hydrogen, deuterium, cyano, $C_1$-$C_4$ alkyl, $C_2$-$C_4$ alkenyl, and $C_2$-$C_4$ alkynyl; wherein the $C_1$-$C_4$ alkyl, $C_2$-$C_4$ alkenyl, or $C_2$-$C_4$ alkynyl is optionally substituted with 1 to 3 substituents each independently selected from the group consisting of deuterium, halogen, hydroxyl, cyano and $C_1$-$C_4$ alkoxy;
Ra is selected from hydrogen, deuterium, halogen, $C_1$-$C_4$ haloalkyl and $C_1$-$C_4$ alkyl; and
Y is selected from $C_1$-$C_4$ alkyl, Cl and Br.

In some embodiments, $R^1$, $R^2$ or $R^{10}$ is hydrogen;

Rx is selected from $C_1$-$C_4$ alkyl, $C_2$-$C_4$ alkenyl, $C_1$-$C_4$ haloalkyl, $C_1$-$C_4$ deuterated alkyl, and $C_1$-$C_4$ alkyl hydroxyl;
Rb is halogen;
k=2, 3 or 4;
Ra is hydrogen, methyl or chlorine;
h=0, 1 or 2; and
Y is Cl or Br.

In some embodiments, Rx is selected from CH=CH$_2$, CH$_2$CF$_3$, CD$_3$ and $C_1$-$C_4$ alkyl hydroxyl;
Rb is fluorine; and
k=2 or 3.

In some embodiments, the compound of the present application is selected from the group consisting of the following compounds:

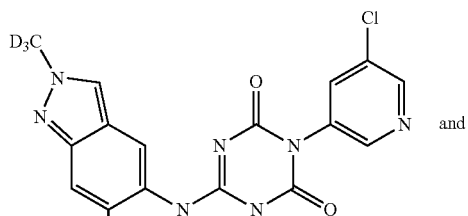

and

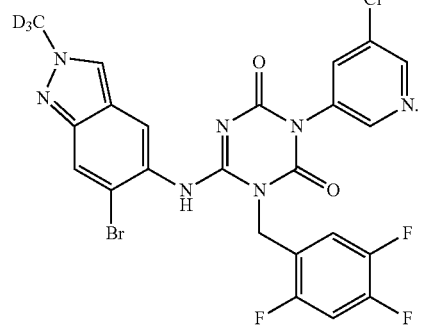

In some embodiments, the compound of the present application is selected from the group consisting of the following compounds:

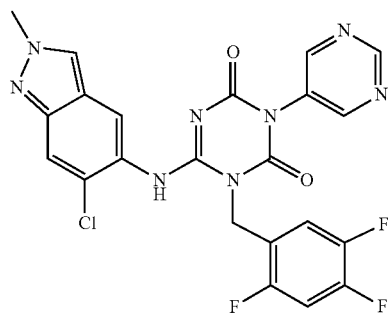 [SMILES: Cn1cc2cc(Nc3nc(=O)n(-c4cncnc4)c(=O)n3Cc3cc(F)c(F)cc3F)c(Cl)cc2n1]

1

-continued

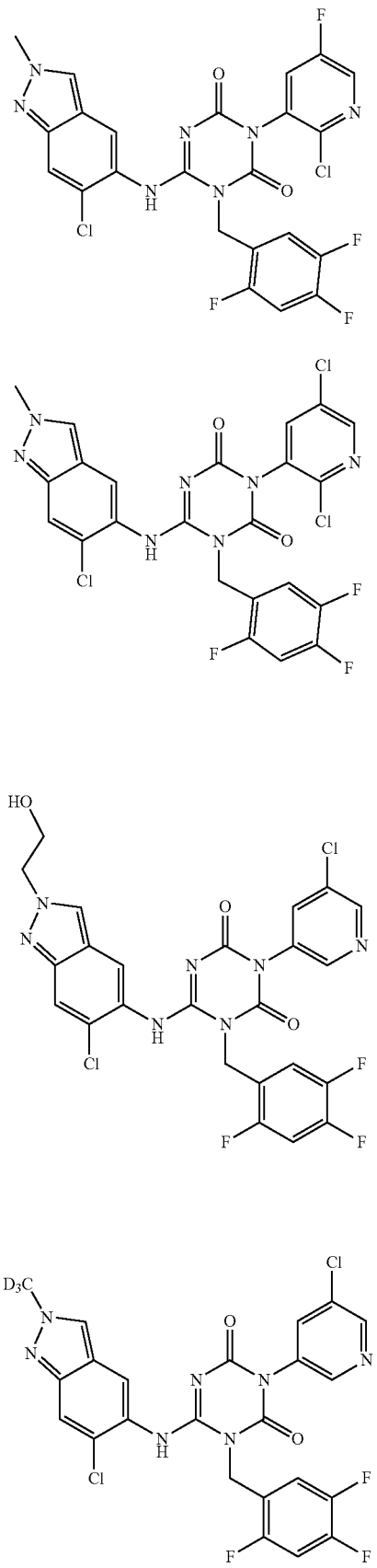

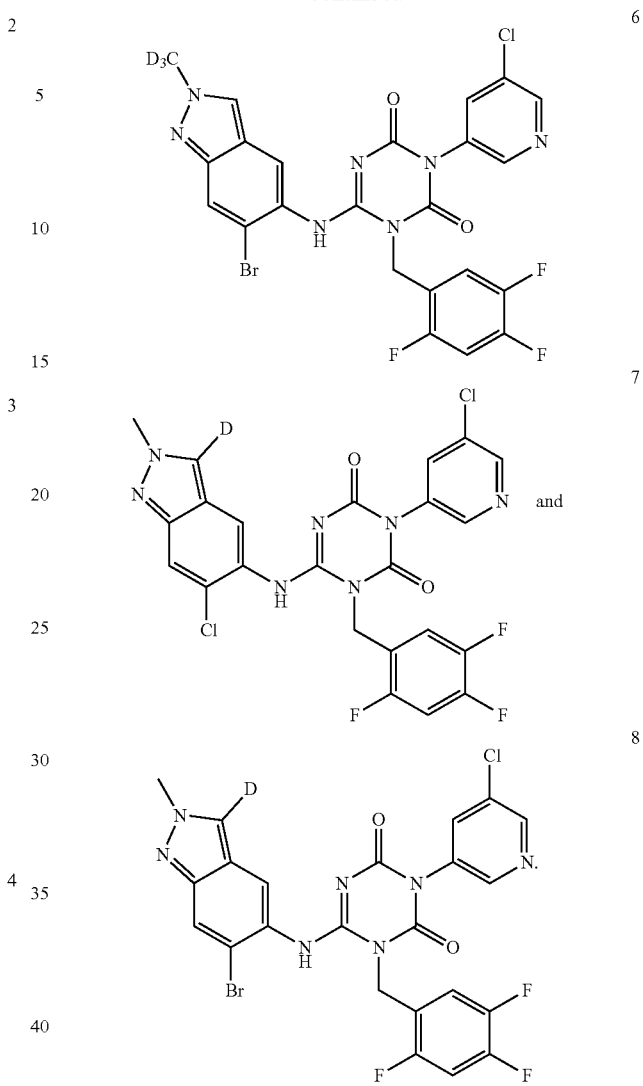

III. Methods of Use

Another aspect of the present application relates to a method for preventing, treating, or ameliorating the symptoms of a viral infection in a subject with a compound of the present application.

In some embodiments, the method comprises the step of administering an effective amount of the compound of the present application to a subject in need thereof.

In some embodiments, the viral infection is a coronavirus infection. In some embodiments, the viral infection is SARS-COV-2 infection.

In certain embodiments, the viral infection is caused by alphavirus, flavivirus, coronavirus, RSV, influenza virus, Powassan virus, ebola virus, or viruses of filoviridae, orthomyxoviridae or paramyxoviridae.

In certain embodiments, the viral infection caused by a virus selected from MERS coronavirus, Eastern equine encephalitis virus, Western equine encephalitis virus, Venezuelan equine encephalitis viruses, Ross River virus, Barmah Forest virus, Powassan virus, Zika virus, and Chikungunya virus.

In some embodiments, the subject is at risk of, exhibiting symptoms of, or diagnosed with, infection of influenza A virus including subtype H1N1, H3N2, H7N9, or H5N1, influenza B virus, influenza C virus, rotavirus A, rotavirus B, rotavirus C, rotavirus D, rotavirus E, human coronavirus, SARS coronavirus, MERS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), Dengue virus, Zika virus, chikungunya, Eastern equine encephalitis virus (EEEV), Western equine encephalitis virus (WEEV), Venezuelan equine encephalitis virus (VEEV), Ross River virus, Barmah Forest virus, yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV), The Human T-lymphotropic virus Type I (HTLV-1), Friend spleen focus-forming virus (SFFV) or Xenotropic MuLVRelated Virus (XMRV). In some embodiments, the subject is at risk of, exhibiting symptoms of, or diagnosed with a Zika virus infection.

In certain embodiments, the subject is diagnosed with influenza A virus including subtypes H1N1, H3N2, H7N9, H5N1 (low path), and H5N1 (high path) influenza B virus, influenza C virus, rotavirus A, rotavirus B, rotavirus C, rotavirus D, rotavirus E, SARS coronavirus, MERS-COV, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, parainfluenza viruses 1 and 3, rinderpest virus, chikungunya, eastern equine encephalitis virus (EEEV), Venezuelan equine encephalitis virus (VEEV), western equine encephalitis virus (WEEV), California encephalitis virus, Japanese encephalitis virus, Rift Valley fever virus (RVFV), hantavirus, Dengue virus serotypes 1, 2, 3 and 4, Zika virus, West Nile virus, Tacaribe virus, Junin, rabies virus, ebola virus, marburg virus, adenovirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV). In certain embodiments, the subject is diagnosed with a Zika virus infection.

In some embodiments, the subject is at risk of, exhibiting symptoms of, or diagnosed with, infection of subgroup 1a or 1b alphacoronaviruses, subgroup 2a, 2b, 2c or 2d betacoronaviruses, or subgroup 3 gammscoronaviruses.

Nonlimiting examples of subgroup 1a alphacoronaviruses and their GenBank Accession Nos. include FCov.FIPV.79.1146.VR.2202 (NV_007025), transmissible gastroenteritis virus (TGEV) (NC_002306; Q811789.2; DQ811786.2; DQ811788.1; DQ811785.1; X52157.1; AJ011482.1; KC962433.1; AJ271965.2; JQ693060.1; KC609371.1; JQ693060.1; JQ693059.1; JQ693058.1; JQ693057.1; JQ693052.1; JQ693051.1; JQ693050.1); porcine reproductive and respiratory syndrome virus (PRRSV) (NC_001961.1; DQ811787), as well as any subtype, clade or sub-clade thereof, including any other subgroup la coronavirus now known (e.g., as can be found in the GenBank® Database) or later identified in the GenBank® Database.

Nonlimiting examples of a subgroup 1b alphacoronaviruses and their GenBank Accession Nos. include HCoV.NL63.Amsterdam.I (NC_005831), BtCoV.HKU2.HK.298.2006 (EF203066), BtCoV.HKU2.HK.33.2006 (EF203067), BtCoV.HKU2.HK.46.2006 (EF203065), BtCoV.HKU2.GD.430.2006 (EF203064), BtCoV.1A.AFCD62 (NC_010437), BtCoV.1B.AFCD307 (NC_010436), BtCov.HKU8.AFCD77 (NC_010438), BtCoV.512.2005 (DQ648858); porcine epidemic diarrhea viruses (NC_003436, DQ355224.1, DQ355223.1, DQ355221.1, JN601062.1, JN601061.1, JN601060.1, JN601059.1, JN601058.1, JN601057.1, JN601056.1, JN601055.1, JN601054.1, JN601053.1, JN601052.1, JN400902.1, JN547395.1, FJ687473.1, FJ687472.1, FJ687471.1, FJ687470.1, FJ687469.1, FJ687468.1, FJ687467.1, FJ687466.1, FJ687465.1, FJ687464.1, FJ687463.1, FJ687462.1, FJ687461.1, FJ687460.1, FJ687459.1, FJ687458.1, FJ687457.1, FJ687456.1, FJ687455.1, FJ687454.1, FJ687453 FJ687452.1, FJ687451.1, FJ687450.1, FJ687449.1, AF500215.1, KF476061.1, KF476060.1, KF476059.1, KF476058.1, KF476057.1, KF476056.1, KF476055.1, KF476054.1, KF476053.1, KF476052.1, KF476051.1, KF476050.1, KF476049.1, KF476048.1, KF177258.1, KF177257.1, KF177256.1, KF177255.1), HCoV.229E (NC_002645), as well as any subtype, clade or sub-clade thereof, including any other subgroup 1b coronavirus now known (e.g., as can be found in the GenBank® Database) or later identified in the GenBank® Database.

Nonlimiting examples of subgroup 2a betacoronaviruses and their GenBank Accession Nos. include HCoV.HKUI.C.N5 (DQ339101), MHV.A59 (NC_001846), PHEV.VW572 (NC_007732), HCoV.OC43.ATCC.VR.759 (NC_005147), bovine enteric coronavirus (BCoV.ENT) (NC_003045), as well as any subtype, clade or sub-clade thereof, including any other subgroup 2a coronavirus now known (e.g., as can be found in the GenBank® Database) or later identified in the GenBank® Database.

Nonlimiting examples of subgroup 2b betacoronaviruses and their GenBank Accession Nos. include human SARS COV-2 isolates, such as Wuhan-Hu-1 (NC_045512.2) and any CoV-2 isolates comprising a genomic sequence set forth in GenBank Accession Nos., such as MT079851.1, MT470137.1, MT121215.1, MT438728.1, MT470115.1, MT358641.1, MT449678.1, MT438742.1, LC529905.1, MT438756.1, MT438751.1, MT460090.1, MT449643.1, MT385425.1, MT019529.1, MT449638.1, MT374105.1, MT449644.1, MT385421.1, MT365031.1, MT385424.1, MT334529.1, MT466071.1, MT461669.1, MT449639.1, MT415321.1, MT385430.1, MT135041.1, MT470179.1, MT470167.1, MT470143.1, MT365029.1, MT114413.1, MT192772.1, MT135043.1, MT049951.1; human SARS COV-1 isolates, such as SARS COV.A022 (AY686863), SARSCOV.CUHK-W1 (AY278554), SARSCOV.GD01 (AY278489), SARSCOV.HC.SZ.61.03 (AY515512), SARSCOV.SZ16 (AY304488), SARSCOV. Urbani (AY278741), SARSCOV.civet010 (AY572035), SARSCOV.MA.15 (DQ497008); bat SARS COV isolates, such as BtSARS.HKU3.1 (DQ022305), BtSARS.HKU3.2 (DQ084199), BtSARS.HKU3.3 (DQ084200), BtSARS.Rml (DQ412043), BtCoV.279.2005 (DQ648857), BtSARS.Rfl (DQ412042), BtCoV.273.2005 (DQ648856), BtSARS.Rp3 (DQ071615),), SARS-COV-2 Delta variants (B.1.617.2 and AY lineages), SARS-COV-2 omicron variants (B.1.1.529), SARS-COV-2 Alpha variants (B.1.1.7 and Q lineages) SARS-COV-2 Beta variants (B.1.351 and descendent lineages), SARS-COV-2 Gamma variants (P.1 and descendent lineages), SARS-COV-2 Epsilon variants (B.1.427 and B.1.429), SARS-COV-2 Eta variants (B.1.525), SARS-COV-2 Iota variants (B.1.526), SARS-COV-2 Kappa variants (B.1.617.1), SARS-COV-2 variants 1.617.3, SARS-CoV-2 Mu variants (B.1.621, B.1.621.1) and SARS-COV-2 Zeta variants (P.2), as well as any subtype, clade or sub-clade thereof, including any other subgroup 2b coronavirus now known (e.g., as can be found in the GenBank® Database) or later identified in the GenBank® Database.

Nonlimiting examples of subgroup 2c betacoronaviruses and their GenBank Accession Nos. include Middle East respiratory syndrome coronavirus (MERS) isolates, such as Riyadh 22012 (KF600652.1), Al-Hasa_18_2013 (KF600651.1), Al-Hasa_17_2013 (KF600647.1), Al-Hasa_152013 (KF600645.1), Al-Hasa_16_2013 (KF600644.1), Al-Hasa_21_2013 (KF600634), Al-Hasa 19_2013 (KF600632), Buraidah_1_2013 (KF600630.1), Hafr-Al-Batin_1_2013 (KF600628.1), Al-Hasa_122013 (KF600627.1), Bisha.ltoreq.1_2012 (KF600620.1), Riyadh_3_2013 (KF600613.1), Riyadh_1_2012 (KF600612.1), Al-Hasa_3_2013 (KF186565.1), Al-Hasa_1_2013 (KF186567.1), Al-Hasa_2_2013 (KF186566.1), Al-Hasa 4_2013 (KF186564.1); Betacoronavirus England 1-N1 (NC_019843), SA-N1 (KC667074); human betacoronavirus 2c Jordan-N3/2012 (KC776174.1); human betacoronavirus 2c EMC/2012, (JX869059.2); any bat coronavirus subgroup 2c isolate, such as bat coronavirus Taper/CII_KSA_287/Bisha/Saudi Arabia (KF493885.1), bat coronavirus Rhhar/CII_KSA 003/Bisha/Saudi Arabia/2013 (KF493888.1), bat coronavirus Pikuh/CII_KSA_001/Riyadh/Saudi Arabia/2013 (KF493887.1), bat coronavirus Rhhar/CII_KSA 002/Bisha/Saudi Arabia/2013 (KF493886.1), bat coronavirus Rhhar/CII_KSA_004/Bisha/Saudi Arabia/2013 (KF493884.1), bat coronavirus BtCoV.HKU4.2 (EF065506), bat coronavirus BtCoV.HKU4.1 (NC_009019), bat coronavirus BtCoV.HKU4.3 (EF065507), bat coronavirus BtCoV.HKU4.4 (EF065508), bat coronavirus BtCoV133.2005 (NC_008315), bat coronavirus BtCoV.HKU5.5 (EF065512), bat coronavirus BtCoV.HKU5.1 (NC_009020), bat coronavirus BtCoV.HKU5.2 (EF065510), bat coronavirus BtCoV.HKU5.3 (EF065511), and bat coronavirus HKU5 isolate (KC522089.1); any additional subgroup 2c, such as KF192507.1, KF600656.1, KF600655.1, KF600654.1, KF600649.1, KF600648.1, KF600646.1, KF600643.1, KF600642.1, KF600640.1, KF600639.1, KF600638.1, KF600637.1, KF600636.1, KF600635.1, KF600631.1, KF600626.1, KF600625.1, KF600624.1, KF600623.1, KF600622.1, KF600621.1, KF600619.1, KF600618.1, KF600616.1, KF600615.1, KF600614.1, KF600641.1, KF600633.1, KF600629.1, KF600617.1, KC869678.2; KC522088.1, KC522087.1, KC522086.1, KC522085.1, KC522084.1, KC522083.1, KC522082.1, KC522081.1, KC522080.1, KC522079.1, KC522078.1, KC522077.1, KC522076.1, KC522075.1, KC522104.1, KC522104.1, KC522103.1, KC522102.1, KC522101.1, KC522100.1, KC522099.1, KC522098.1, KC522097.1, KC522096.1, KC522095.1, KC522094.1, KC522093.1, KC522092.1, KC522091.1, KC522090.1, KC522119.1, KC522118.1, KC522117.1, KC522116.1, KC522115.1, KC522114.1, KC522113.1, KC522112.1, KC522111.1, KC522110.1, KC522109.1, KC522108.1, KC522107.1, KC522106.1, KC522105.1); Pipistrellus bat coronavirus HKU4 isolates (KC522048.1, KC522047.1, KC522046, 1, KC522045.1, KC522044.1, KC522043.1, KC522042.1, KC522041.1, KC522040.1, KC522039.1,, KC522038.1,, KC522037.1, KC522036.1,, KC522048.1, KC522047.1, KC522046.1, KC522045.1, KC522044.1, KC522043.1, KC522042.1, KC522041.1, KC522040, 1, KC522039.1, KC522038.1, KC522037.1, KC522036.1, KC522061.1, KC522060.1, KC522059.1, KC522058.1, KC522057.1, KC522056.1, KC522055.1, KC522054.1, KC522053.1, KC522052.1, KC522051.1, KC522050.1, KC522049.1, KC522074.1, KC522073.1, KC522072.1, KC522071.1, KC522070.1, KC522069.1, KC522068.1, KC522067.1, KC522066.1, KC522065.1, KC522064.1, KC522063.1, KC522062.1), as well as any subtype, clade or sub-clade thereof, including any other subgroup 2c coronavirus now known (e.g., as can be found in the GenBank® Database) or later identified in the GenBank® Database.

Nonlimiting examples of subgroup 2d betacoronaviruses and their GenBank Accession Nos. include BtCoV.HKU9.2 (EF065514), BtCoV.HKU9.1 (NC_009021), BtCoV.HKU9.3 (EF065515), BtCoV.HKU9.4 (EF065516), as well as any subtype, clade or sub-clade thereof, including any other subgroup 2d coronavirus now known (e.g., as can be found in the GenBank® Database) or later identified in the GenBank® Database.

Nonlimiting examples of subgroup 3 gammacoronaviruses include IBV.Beaudette.IBV.p65 (DQ001339) or any other subgroup 3 coronavirus now known (e.g., as can be found in the GenBank® Database) or later identified in the GenBank® Database.

A coronavirus defined by any of the isolates or genomic sequences in the aforementioned subgroups 1a, 1b, 2a, 2b, 2c, 2d and 3 can be targeted for decontamination in accordance with the methods and compositions of the present application.

In certain embodiments, the subject is diagnosed with gastroenteritis, acute respiratory disease, severe acute respiratory syndrome, post-viral fatigue syndrome, viral hemorrhagic fevers, acquired immunodeficiency syndrome or hepatitis.

In some embodiments, the compound of the present application is administered orally or by inhalation. In certain embodiments, the compound is administered by inhalation through the lungs.

In some embodiments, the compound of the present application is administered at a daily dosage in the range of 10-8000 mg,, 20-400 mg, 20-200 mg, 20-100 mg, 20-80 mg, 20-40 mg, 40-8000 mg, 40-4000 mg, 40-2000 mg, 40-1000 mg, 40-800 mg, 40-400 mg, 40-200 mg, 40-100 mg, 40-80 mg, 80-8000 mg, 80-4000 mg, 80-2000 mg, 80-1000 mg, 80-800 mg, 80-400 mg, 80-200 mg, 80-100 mg, 100-8000 mg, 100-4000 mg, 100-2000 mg, 100-1000 mg, 100-800 mg, 100-400 mg, 100-200 mg, 200-8000 mg, 200-4000 mg, 200-2000 mg, 200-1000 mg, 200-800 mg, 200-400 mg, 400-8000 mg, 400-4000 mg, 400-2000 mg, 400-1000 mg, 400-800 mg, 800-8000 mg, 800-4000 mg, 800-2000 mg, 800-1000 mg, 1000-8000 mg, 1000-4000 mg, 1000-2000 mg, 2000-8000 mg, 2000-4000 mg, or 4000-8000 mg.

In some embodiments, the compound of the present application is administered at a daily dosage in the range of 50-1000 mg, 100-800 mg.

IV. Pharmaceutical Compositions

Another aspect of the present application relates to a pharmaceutical composition comprising a compound of the present application. In some embodiments, the pharmaceutical composition comprises a compound of the present application and a pharmaceutically acceptable carrier.

In some embodiments, the pharmaceutical composition comprises, or is in the form of, a pharmaceutically acceptable salt of the compound of the present application, as generally described below. Examples of suitable pharmaceutically acceptable organic and/or inorganic acids that may form a salt with a compound of the present application include, but are not limited to, hydrochloric acid, hydrobromic acid, sulfuric acid, nitric acid, acetic acid and citric acid, as well as other pharmaceutically acceptable acids known per se (for which reference is made to the references referred to below).

When a compound of the present application contain an acidic group as well as a basic group, the compound can form internal salts, which can also be used in the compositions and methods described herein. When a compound of the present application contains a hydrogen-donating heteroatom (e.g., NH), salts are contemplated to cover isomers formed by transfer of said hydrogen atom to a basic group or atom within the molecule.

Pharmaceutically acceptable salts of the compounds of the present application include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

Physiologically acceptable salts of the compounds of the present application are those that are formed internally in a subject administered compound for the treatment or prevention of disease. Suitable salts include those of lithium, sodium, potassium, magnesium, calcium, manganese, bile salts.

The compounds of the present application can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

In some embodiments, the pharmaceutical composition of the present application comprises an effective amount of a compound of the present application and a pharmaceutically acceptable carrier. Generally, for pharmaceutical use, the compound of the present application can be formulated as a pharmaceutical preparation comprising at least one compound and at least one pharmaceutically acceptable carrier, diluent or excipient and/or adjuvant, and optionally one or more further pharmaceutically active compounds. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. The disclosed pharmaceutical compositions can be in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain from 1 and 1000 mg, and usually from 5 and 500 mg, of the at least one compound of the disclosure, e.g., about 50, 100, 200, 250, 300, 350, 400, 450, 500, 550, 600, 650, 700, 750 or 800 mg per unit dosage.

The compound or pharmaceutical composition of the present application can be administered by a variety of routes including the oral, ocular, rectal, transdermal, subcutaneous, intravenous, intramuscular or intranasal routes, depending mainly on the specific preparation used. The compound or pharmaceutical composition will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be from 0.01 to 1000 mg per kilogram body weight of the patient per day, more often from 0.1 and 500 mg, such as from 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the pharmaceutical composition described herein can be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. In certain embodiments, the formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition, which can include plasticizers, pigments, colorants, stabilizing agents, and glidants. Delayed release, extended release, and/or pulsatile release dosage formulations can be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa .: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT™M (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER™ 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The concentration of the compound of the present application can vary from about 0.5 to about 100 wt. % (weight percent) of the final pharmaceutical composition. For oral use, the pharmaceutical composition can generally contain from about 5 to about 100% by weight of the active material.

For other uses, the pharmaceutical composition can generally have from about 0.5 to about 50 wt. % of the active material.

The compositions described herein can be formulated for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and CARBOPOL™ 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In some embodiments, the acrylic polymer is an acrylic resin lacquer such as that which is commercially available from Rohm Pharma under the trade name EUDRAGIT. In further preferred embodiments, the acrylic polymer comprises a mixture of two acrylic resin lacquers commercially available from Rohm Pharma under the trade names EUDRAGIT RL30D and EUDRAGIT RS30D, respectively. EUDRAGIT RL30D and EUDRAGIT RS30D are copolymers of acrylic and methacrylic esters with a low content of quaternary ammonium groups, the molar ratio of ammonium groups to the remaining neutral (meth)acrylic esters being 1:20 in EUDRAGIT RL30D and 1:40 in EUDRAGIT RS30D. The mean molecular weight is about 150,000. EUDRAGIT S-100 and EUDRAGIT L-100 are also preferred. The code designations RL (high permeability) and RS (low permeability) refer to the permeability properties of these agents. EUDRAGIT RL/RS mixtures are insoluble in water and in digestive fluids. However, multiparticulate systems formed to include the same are swellable and permeable in aqueous solutions and digestive fluids.

The polymers described above such as EUDRAGIT RL/RS can be mixed together in any desired ratio in order to ultimately obtain a sustained-release formulation having a desirable dissolution profile. Desirable sustained-release multiparticulate systems can be obtained, for instance, from 100% EUDRAGIT RL, 50% EUDRAGIT RL and 50% EUDRAGIT RS, and 10% EUDRAGIT RL and 90% EUDRAGITRS. One skilled in the art will recognize that other acrylic polymers can also be used, such as, for example, EUDRAGIT L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spraycongealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastro-intestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trade name EUDRAGIT™ (Rohm Pharma; Westerstadt, Germany), including EUDRAGIT™ L30D-55 and L100-55 (soluble at pH 5.5 and above), EUDRAGIT™ L-100 (soluble at pH 6.0 and above), EUDRAGIT™ S (soluble at pH 7.0 and above, as a result of a higher degree of esterification), and EUDRAGIT™ NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses can be designed.

The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit can comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or cannot include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

In one embodiment, the compound of the present application is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid can include a lipophilic component, an aqueous component or both. Some emulsions can be gels or otherwise include a gel component. Some gels, however, are not emulsions because they do not contain a homogenized blend of immiscible components. Methods for preparing lotions, creams, ointments, and gels are well known in the art.

V. Combination Therapies

The compound described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics, anti-narcoleptics, and antiviral agents.

Examples of antiviral agents include, but are not limited to, RNA-dependent RNA polymerase (RdRp) inhibitors, protease drugs, anti-viral neutralizing antibodies and other antiviral drugs. In a particular embodiment, the antiviral agent is a non-CNS targeting antiviral compound. "Adjunctive administration", as used herein, means the compound can be administered in the same dosage form or in separate dosage forms with one or more other active agents. The additional active agent(s) can be formulated for immediate release, controlled release, or combinations thereof.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

In certain embodiments, the exemplary compounds and pharmaceutical compositions can be administered in combination with another antiviral agent(s) such as abacavir, acyclovir, acyclovir, adefovir, amantadine, amprenavir, ampligen, arbidol, atazanavir, atripla, balapiravir, BCX4430, boceprevir, cidofovir, combivir, daclatasvir, darunavir, dasabuvir, delavirdine, didanosine, docosanol, edoxudine, efavirenz, emtricitabine, enfuvirtide, entecavir, famciclovir, favipiravir, fomivirsen, fosamprenavir, foscarnet, fosfonet, ganciclovir, GS-5734, ibacitabine, imunovir, idoxuridine, imiquimod, indinavir, inosine, interferon type III, interferon type II, interferon type I, lamivudine, ledipasvir, lopinavir, loviride, maraviroc, moroxydine, methisazone, nelfinavir, nevirapine, nexavir, NITD008, ombitasvir, oseltamivir, paritaprevir, peginterferon alfa-2a, penciclovir, peramivir, pleconaril, podophyllotoxin, raltegravir, ribavirin, rimantadine, ritonavir, pyramidine, saquinavir, simeprevir, sofosbuvir, stavudine, telaprevir, telbivudine, tenofovir, tenofovir disoproxil, Tenofovir Exalidex, tipranavir, trifluridine, trizivir, tromantadine, truvada, valaciclovir, valganciclovir, vicriviroc, vidarabine, viramidine zalcitabine, zanamivir, or zidovudine and combinations thereof.

Although a particular embodiment of the invention has been described in detail for purposes of illustration, various modifications and enhancements may be made without departing from the spirit and scope of the invention. Accordingly, the invention is not to be limited except as by the appended claims.

EXAMPLES

Example 1: Synthesis

The compounds of the disclosure may be prepared using methods disclosed herein and routine modifications thereof which will be apparent given the disclosure herein and methods well known in the art. Conventional and well-known synthetic methods may be used in addition to the teachings herein.

The synthesis of typical compounds of formula (I), or a pharmaceutically acceptable salt thereof, e.g., compounds having structures described by one or more of formula (I), or other formulas or compounds disclosed herein, may be accomplished as described in the following examples.
General Syntheses Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group The identity of the final product will generally render apparent the identity of the necessary starting materials by a simple process of inspection, given the examples herein. Group labels (e.g., R1, R2) used in the reaction schemes herein are for illustrative purposes only and unless otherwise specified do not necessarily match by name or function the labels used elsewhere to describe compounds of formula (I) or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers.

Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), N, N-dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the purview of one skilled in the art.

In another aspect, the present invention provides a method for preparing a compound of the formula (I), a pharmaceutically acceptable salt, an ester or a stereoisomer thereof. In some embodiments, the method comprises the reaction steps of Route 1.

Route 1:

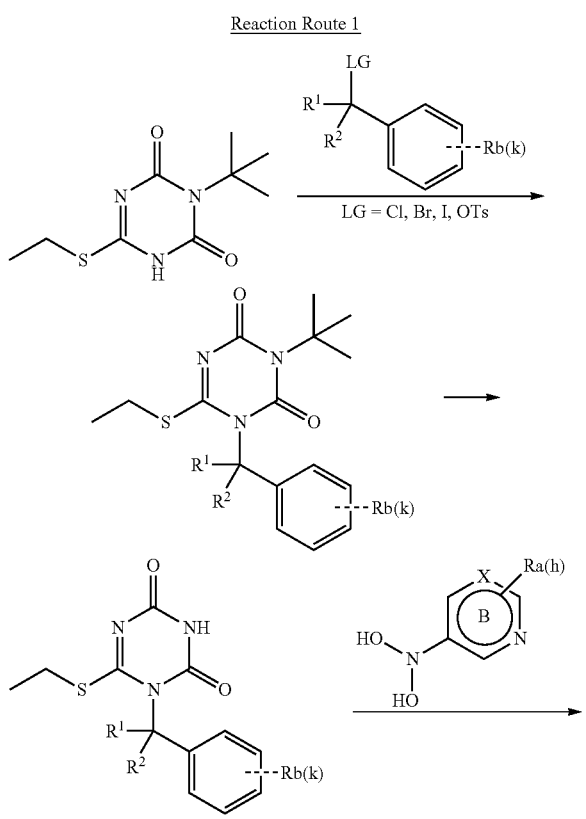

Reaction Route 1

-continued

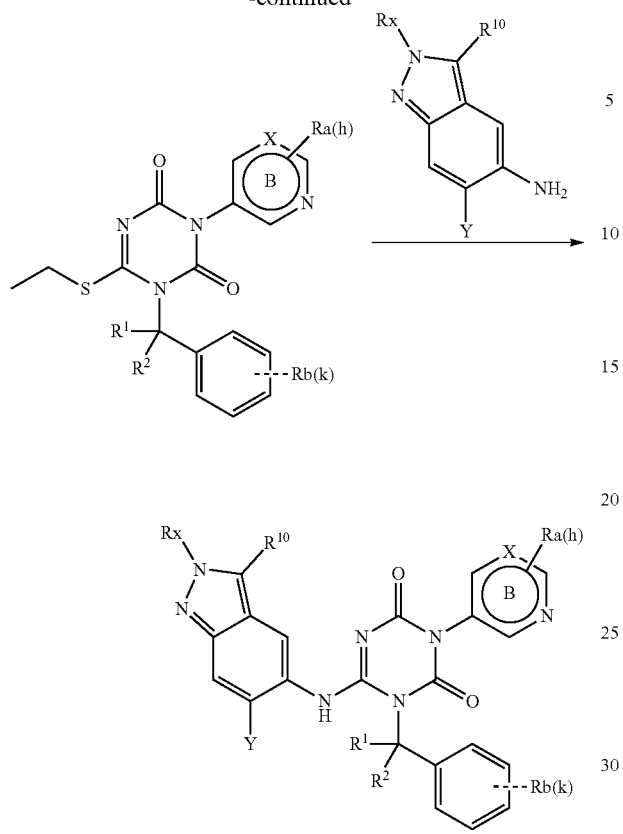

I

In Reaction Route 1, the structure of each group is as defined in this disclosure. The compounds can all exist in the form of stereoisomers, cis-trans isomers, tautomers or mixtures thereof.

Hereinafter, the present disclosure will be explained in detail through the following examples in order to better understand various aspects of the present disclosure and its advantages. However, it should be understood that the following examples are non-limiting and serve only to illustrate certain embodiments of the present disclosure.

PROCEDURE

Although any person skilled in the art can prepare the compounds of the present application accordance with the general techniques disclosed above, for convenience, more detailed synthesis techniques of the compounds of the present application are provided. Additionally, all reagents and reaction conditions used in the synthesis are known to those skilled in the art and can be obtained from common commercial sources. For example, various reagents including deuterated reagents used in the examples are available from Sigma-Aldrich Company Ltd.

Unless otherwise stated,[1] HNMR is measured using deuterated dimethyl sulfoxide at a frequency of 500 MHz at about 20-30° C. Use standard NMR abbreviations: s=unimodal; d=bimodal; dd=bimodal bimodal; t=triple; q=quadruple; p=quintuple; m=multimodal; br=broadband.

Procedure 1: Preparation of 6-((6-chloro-2-methyl-2H-indazol-5-yl)amino)-3-(pyrimidin-5-yl)-1-(2,4,5-trifluorobenzyl)-1,3,5-triazine-2,4(1H,3H)-dione (1)

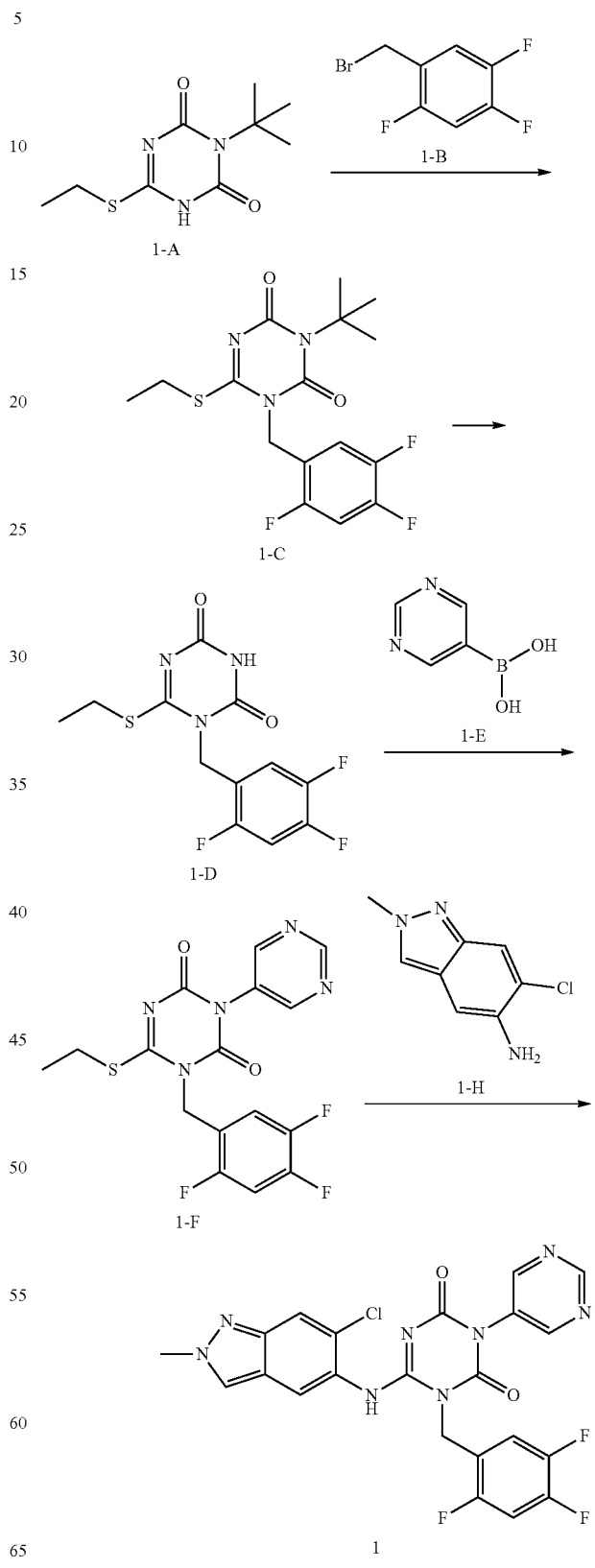

(1) Synthesis of Compound 1-C

Compound 1-A (1 g, 4.36 mmol) was dissolved in acetonitrile (25 mL), and potassium carbonate (0.8 g, 5.79 mmol) and compound 1-B (1.10 g, 4.82 mmol) were added to the above solution and heated to reflux for 3 h. The reaction solution was diluted with ethyl acetate and filtered, and the filtrate was concentrated and purified by column chromatography to produce compound 1-C (1.6 g, 98%).

(2) Synthesis of Compound 1-D

Compound 1-C (1.6 g, 4.29 mmol) was added to TFA (15 mL), stirred at room temperature overnight, concentrated, pulsed with isopropyl ether, filtered, collected and dried to yield Compound 1-D (1.16 g, 85%).

(3) Synthesis of Compound 1-F

Compound 1-D (500 mg, 1.58 mmol), compound 1-E (234 mg, 1.89 mmol), anhydrous copper acetate (315 mg, 1.57 mmol), pyridine (373 mg, 4.73 mmol) and triethylamine (478 mg, 4.73 mmol) in dichloroethane (5 ml) were stirred at room temperature with open mouth for 16 h. The compound 1-F was directly separated by 1-F (160 mg, 26%) was separated directly by column chromatography.

(4) Synthesis of Compound 1

To a tetrahydrofuran solution of compound 1-F (700 mg, 1.75 mmol) and 6-chloro-2-methyl-2H-indazol-5-amine (354 mg, 1.93 mmol) was added tetrahydrofuran solution of LiHMDS (1M, 2.1 mL, 2.1 mmol) dropwise at 0° C., maintained at 0° C. for 3 h, and then transferred to room temperature and stirred for 40 min. After the reaction was completed, the reaction was quenched by adding saturated ammonium chloride solution (10 mL), extracted with ethyl acetate (10 mL×3), combined the organic phases, washed with saturated saline, dried with anhydrous Na2SO4, filtered, concentrated and purified by column chromatography to produce compound 1.

Other compounds are synthesized as in the preparation of Example 1, simply by replacing the corresponding raw materials.

The following compounds were prepared according to the procedures described herein (and indicated in Table 1 under Procedure) using the appropriate starting material(s) and appropriate protecting group chemistry as needed.

TABLE 1

| No. | Structure | ES/MS(m/z, M + H⁺) | ¹H NMR |
|---|---|---|---|
| 1 | 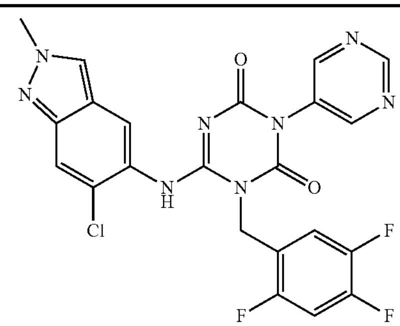 | 515.1 | δ 9.00 (d, J = 1.7 Hz, 2H), 8.80 (d, J = 1.7 Hz, 1H), 8.12 (d, J = 1.7, 1H), 8.00 (d, J = 1.8 Hz, 1H), 7.58 (d, J = 0.6 Hz, 1H), 7.20-7.16 (m, 1.0 Hz, 1H), 7.03-7.00 (m, 1H), 5.25 (d, J = 1.0 Hz, 2H), 3.93 (s, 3H). |
| 2 | 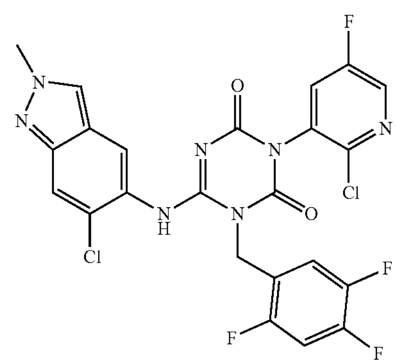 [SMILES: Cn1cc2cc(Nc3nc(=O)n(-c4cc(F)cnc4Cl)c(=O)n3Cc3cc(F)c(F)cc3F)c(Cl)cc2n1] | 566.0 | δ 8.12 (d, J = 1.7, 1H), 8.06 (d, J = 8.0, 1H), 8.00 (d, J = 1.8 Hz, 1H), 7.79 (d, J = 8.0, 1H), 7.58 (d, J = 0.6 Hz, 1H), 7.20-7.16 (m, 1.0 Hz, 1H), 7.03-7.00 (m, 1H), 5.25 (d, J = 1.0 Hz, 2H), 3.93 (s, 3H) |
| 3 | 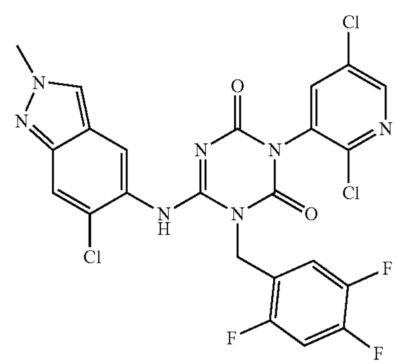 | 582.0 | δ 8.17 (d, J = 1.6 Hz, 1H), 8.12 (d, J = 1.7 Hz, 1H), 7.77 (d, J = 1.7 Hz, 1H), 7.61-7.52 (m, 2H), 7.30-7.22 (m, 1H), 7.16-7.12 (m, 1H), 5.28 (d, J = 1.0 Hz, 2H), 3.93 (s, 3H) |

TABLE 1-continued

| No. | Structure | ES/MS(m/z, M + H⁺) | ¹H NMR |
|---|---|---|---|
| 4 | 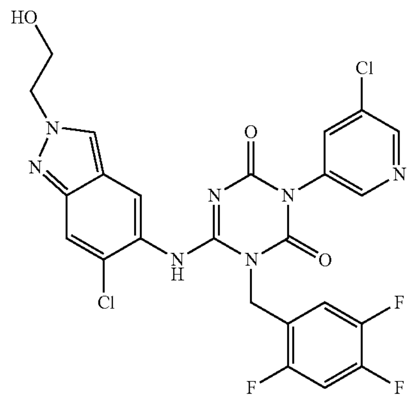 [SMILES: O=c1nc(Nc2cc3cn(CCO)nc3cc2Cl)n(Cc2cc(F)c(F)cc2F)c(=O)n1-c1cncc(Cl)c1] | 578.0 | δ 8.76 (d, J = 1.3 Hz, 1H), 8.33 (d, J = 1.2 Hz, 1H), 7.79 (s, 1H), 7.71 (d, J = 0.6 Hz, 1H), 7.67 (d, J = 0.6 Hz, 1H), 7.63-7.56 (m, 1H), 7.40-7.30 (m, 1H), 7.12 (s, 1H), 5.11 (d, J = 1.0 Hz, 2H), 4.82-4.79 (m, 1H), 4.03 (s, 2H), 3.87 (s, 2H), 2.44 (s, 3H). |
| 5 | 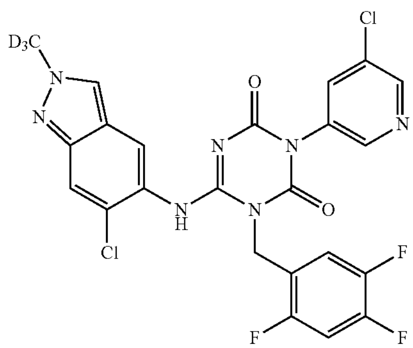 | 551.0 | δ 8.93 (s, 1H), 8.79 (s, 1H), 8.57-8.46 (m, 2H), 8.42 (s, 1H), 7.48 (s, 1H), 7.19 (s, 1H), 7.12-7.05 (m, 1H), 7.05-7.01 (m, 1H), 4.95 (s, 2H). |
| 6 | 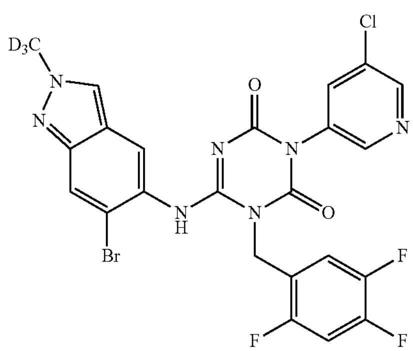 [SMILES: [2H]C([2H])([2H])n1cc2cc(Nc3nc(=O)n(-c4cncc(Cl)c4)c(=O)n3Cc3cc(F)c(F)cc3F)c(Cl)cc2n1] | 595.0 | δ 8.93 (s, 1H), 8.79 (s, 1H), 8.57-8.46 (m, 2H), 8.41 (s, 1H), 7.46 (s, 1H), 7.19 (s, 1H), 7.10-7.05 (m, 1H), 7.05-7.00 (m, 1H), 4.95 (s, 2H). |
| 7 | 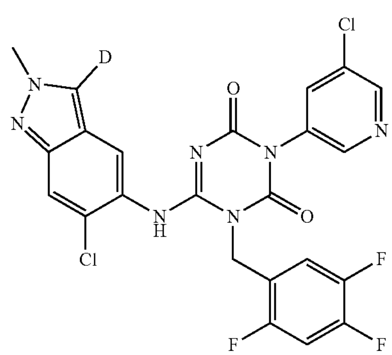 [SMILES: [2H]c1c2cc(Nc3nc(=O)n(-c4cncc(Cl)c4)c(=O)n3Cc3cc(F)c(F)cc3F)c(Cl)cc2nn1C] | 549.1 | δ 8.93 (s, 1H), 8.79 (s, 1H), 8.57-8.46 (m, 2H), 7.48 (s, 1H), 7.19 (s, 1H), 7.12-7.05 (m, 1H), 7.05-7.01 (m, 1H), 4.95 (s, 2H), 3.95 (s, 3H). |

TABLE 1-continued

| No. | Structure | ES/MS(m/z, M + H⁺) | ¹H NMR |
|---|---|---|---|
| 8 | [structure: 2-methyl-indazole with Br substituent, linked via NH to triazine-trione core bearing 5-chloropyridin-3-yl and 2,4,5-trifluorobenzyl groups] | 592.0 | δ 8.93 (s, 1H), 8.79 (s, 1H), 8.57-8.46 (m, 2H), 7.46 (s, 1H), 7.19 (s, 1H), 7.10-7.05 (m, 1H), 7.05-7.00 (m, 1H), 4.95 (s, 2H), 3.93 (s, 3H). |

Biological Example 1

In vitro pharmacodynamic assay of antiviral potency of potential antiviral compounds against SARS-COV-2.

1. Purpose

To evaluate the in vitro antiviral activity of potential antiviral compounds against SARS-COV-2 Omicron hCoV-19/USA/MD HP20874/2021 (B.1.1.529) strain and hCoV-19/USA/Chicago IL/2022 (BA.5.2) in vitro cellular infection system.

2. Materials 2.1 Reference Compounds

The reference compound, ridacivir, was provided by IITRI. 8 concentration points and 3 multiple pores were set up to analyze the compound with the reference remdesivir.

2.2 Cell Lines

Human lung cancer cell line Calu-3 cells were cultured in Minimal Essential Medium (EMEM) containing 10% heat inactivated fetal bovine serum (Gibco, item number A3840001), 100 U/ml penicillin and streptomycin.

2.3 Reagents and Instruments

The main reagents used in this assay were anti-coronavirus nucleoprotein (NP) monoclonal antibody, peroxidase-conjugated goat anti-mouse IgG, and ABTS peroxidase.

The main instruments used in this assay were enzyme marker and ELISA plate reader.

3. Methods

Calu-3 cells were seeded in 96-well plates with different dilution concentrations of compounds, and Omicron variant virus strain with MOI=0.01 was added at the same time. The supernatant containing the virus was washed after 1 hour of incubation, replaced with a medium containing a ploidy dilution compound, and incubated for 48 hours in a humidified chamber at 37±2° C. with 5±2% CO2.

The absorbance readings for each well were collected via SoftMaxPro software and imported into a Microsoft Excel spreadsheet for further calculations. Outliers are detected by the built-in Grubbs test in Graphpad Prism 9. For each well, the percent virus reduction (PVR) was calculated using the formula and the half inhibition concentration (EC50) was calculated by fitting a 4-parameter nonlinear regression curve to the concentration-response curve for each donor.

Result:

| Compound number | hCoV-19/ USA/MD HP20874/2021 (B.1.1.529) in Calu 3 EC50 (nM) | hCoV-19/ USA/Chicago IL/2022 (BA.5.2) in Calu 3 EC50 (nM) |
|---|---|---|
| 1 | 195 | 323 |
| 2 | 98 | 156 |
| 3 | 84 | 149 |
| 4 | 13 | 18 |
| 5 | 9 | 15 |
| 6 | 10 | 20 |

Biological Example 2: Pharmacokinetic Properties Testing in Rat Model

Oral administration: The compound was administered with a volume ratio of Solutol:PEG400:Tween80:Saline=10:40:2:48 (v/v/v) at a dose of 10 mg/kg. At 0.25 h, 0.5 h, 1 h, 2 h, 4 h, 8 h, 10 h, 12 h and 24 h after drug administration, blood was serially collected from the fundus venous plexus in EP tubes containing EDTA, centrifuged at 8000 rpm/min for 5 min and then the upper layer of plasma was frozen at −80° C. and stored for LC-MS/MS analysis.

Intravenous administration: the compound was administered with a volume ratio of 10% DMSO/30% PEG400/60% water (v/v/v) at a dose of 1 mg/kg). At 0.0833 h, 0.25 h, 0.5 h, 1 h, 2 h, 4 h, 8 h, 12 h and 24 h after drug administration, blood was serially collected from the fundic venous plexus in EP tubes containing EDTA, centrifuged at 8000 rpm/min for 5 min and then the upper layer of plasma was frozen at −80° C. and stored for LC-MS/MS analysis.

The pharmacokinetic parameters were calculated from the blood concentration-time data obtained from the tests using WinNonlin software.

TABLE 1

Summary of pharmacokinetic data in rats

| Compound number | Intravenous injection AUClast (h ng/mL) | Oral AUClast (h ng/mL) |
|---|---|---|
| 4 | 2040 | 10800 |
| 5 | 18968 | 224111 |
| 6 | 19543 | 204871 |

Biological Example 3: Pharmacokinetic Property Testing in Crab-Eating Monkeys Oral administration: The compounds were administered with a volume ratio of Solutol:PEG400:Tween80:Saline=10:40:2:48 (v/v/v/v) at a dose of 2 mg/kg. At 0.25 h, 0.5 h, 1 h, 2 h, 4 h, 8 h, 10 h, 12 h and 24 h after drug administration, blood was serially collected from the fundus venous plexus in EP tubes containing EDTA, centrifuged at 8000 rpm/min for 5 min and then the upper layer of plasma was frozen at −80° C. and stored for LC-MS/MS analysis.

Intravenous administration: the compound was administered with 10% DMSO/30% PEG400/60% water (v/v/v) at a dose of 1 mg/kg). At 0.0833 h, 0.25 h, 0.5 h, 1 h, 2 h, 4 h, 8 h, 12 h and 24 h after drug administration, blood was serially collected from the fundic venous plexus in EP tubes containing EDTA, centrifuged at 8000 rpm/min for 5 min and then the upper layer of plasma was frozen at −80° C. and stored for LC-MS/MS analysis.

The pharmacokinetic parameters were calculated from the blood concentration-time data obtained from the tests using WinNonlin software.

TABLE 1

Summary of pharmacokinetic data of crab-eating monkeys.

| Compound number | Intravenous injection AUClast (h ng/mL) | Oral AUClast (h ng/mL) |
|---|---|---|
| 4 | 10300 | 15212 |
| 5 | 38439 | 60731 |
| 6 | 35660 | 58972 |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A compound of Formula I

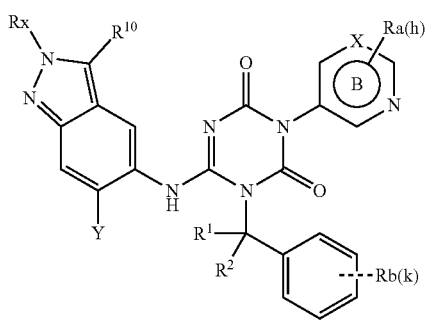

pharmaceutically acceptable salts thereof, deuterium substitutes thereof, isomers thereof, and prodrugs thereof, wherein $R^1$, $R^2$ or $R^{10}$ is independently selected from hydrogen, halogen, and deuterium;

Rx is selected from the group consisting of hydrogen, deuterium, cyano, alkyl, alkenyl, and alkynyl; wherein the alkyl, alkenyl, or alkynyl is optionally substituted with 1 to 3 substituents each independently selected from the group consisting of deuterium, halogen, hydroxyl, cyano, and alkoxy;

Rb is selected from the group consisting of hydrogen, deuterium, halogen, and cyano;

k=2, 3 or 4;

B ring is a six-membered heteroaromatic ring containing N and is substituted with h number of Ra;

Ra is selected from the group consisting of hydrogen, deuterium, halogen, haloalkyl and alkyl;

h=0, 1 or 2;

X is C or N; and

Y is selected from the group consisting of alkyl, Cl and Br, with the proviso that the compound of Formula I is not

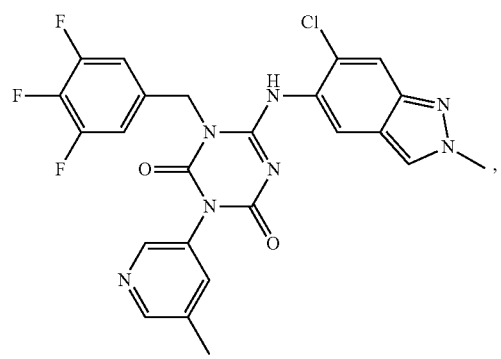

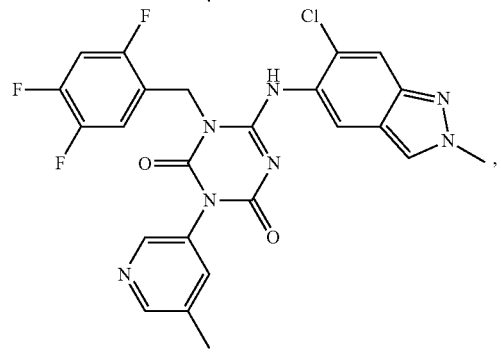

41
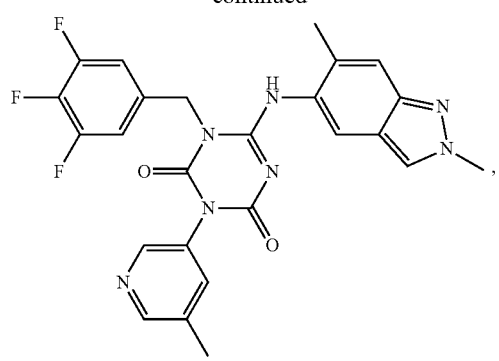
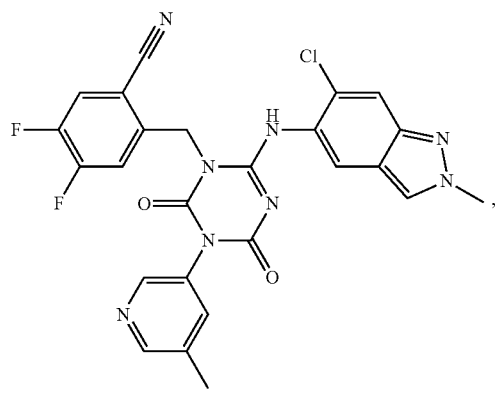
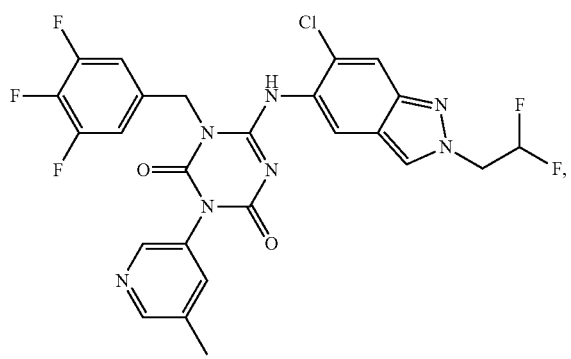
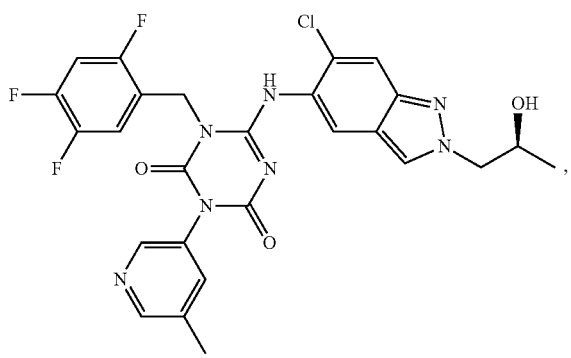
42
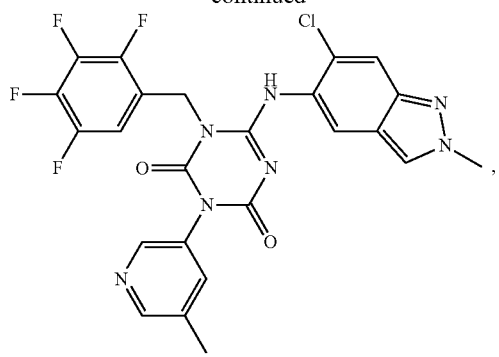
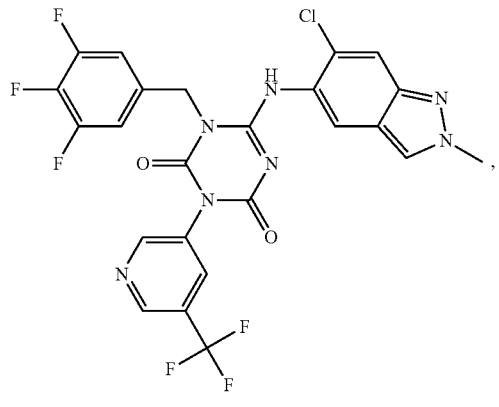
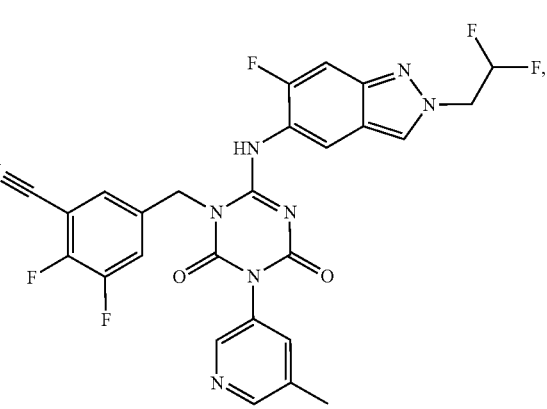
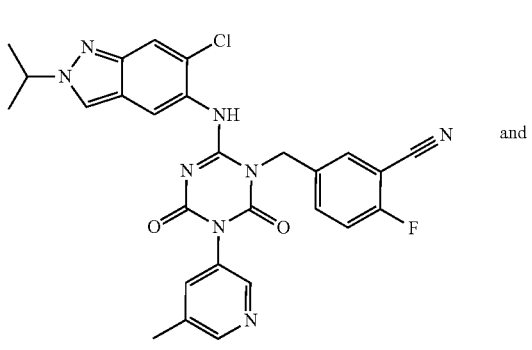
and

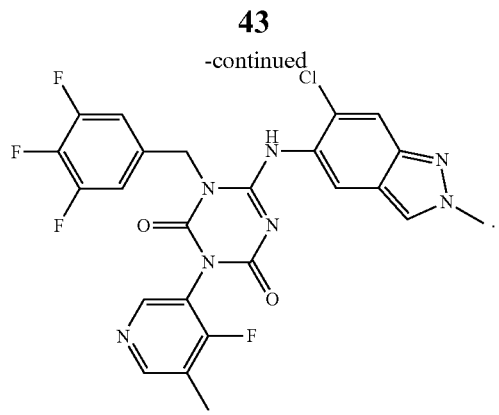

2. The compound of claim 1, pharmaceutically acceptable salts thereof, deuterium substitutes thereof, isomers thereof, and prodrugs thereof, wherein Ra is selected from the group consisting of hydrogen, deuterium, halogen; and wherein h=0, 1 or 2.

3. The compound of claim 1, pharmaceutically acceptable salts thereof, deuterium substitutes thereof, isomers thereof, and prodrugs thereof, wherein Rx is selected from the group consisting of hydrogen, deuterium, cyano, $C_1$-$C_4$ alkyl, $C_2$-$C_4$ alkenyl, and $C_2$-$C_4$ alkynyl; wherein the $C_1$-$C_4$ alkyl, $C_2$-$C_4$ alkenyl, and $C_2$-$C_4$ alkynyl are optionally substituted with 1 to 3 substituents each independently selected from the group consisting of deuterium, halogen, hydroxyl, cyano, and $C_1$-$C_4$ alkoxy;

Ra is selected from the group consisting of hydrogen, deuterium, halogen, $C_1$-$C_4$ haloalkyl and $C_1$-$C_4$ alkyl; and Y is selected from the group consisting of $C_1$-$C_4$ alkyl, Cl and Br.

4. The compound of claim 1, pharmaceutically acceptable salts thereof, deuterium substitutes thereof, isomers thereof, and prodrugs thereof, wherein $R^1$, $R^2$ and $R^{10}$ are hydrogen;

Rx is selected from the group consisting of $C_1$-$C_4$ alkyl, $C_2$-$C_4$ alkenyl, $C_1$-$C_4$ haloalkyl, $C_1$-$C_4$ deuterated alkyl, and $C_1$-$C_4$ alkyl hydroxyl;

Rb is halogen;

k=2, 3 or 4;

Ra is selected from the group consisting of hydrogen, methyl and chlorine;

h=0, 1 or 2; and

Y is Cl or Br.

5. The compound of claim 1, pharmaceutically acceptable salts thereof, deuterium substitutes thereof, isomers thereof, and prodrugs thereof, wherein Rx is selected from the group consisting of CH=$CH_2$, $CH_2CF_3$, $CD_3$ and $C_1$-$C_4$ alkyl hydroxyl;

Rb is fluorine; and k=2 or 3.

6. A compound, pharmaceutically acceptable salts thereof, deuterium substitutes thereof, isomers thereof, and prodrugs thereof, wherein the compound is selected from the group consisting of

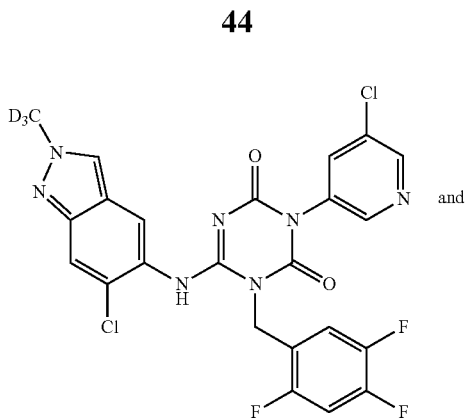

and

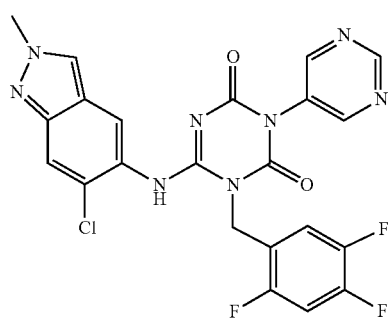

7. A compound, pharmaceutically acceptable salts thereof, deuterium substitutes thereof, isomers thereof, and prodrugs thereof, wherein the compound is selected from the group consisting of

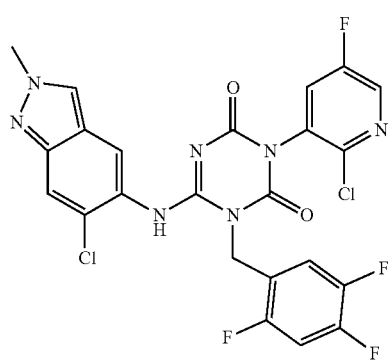

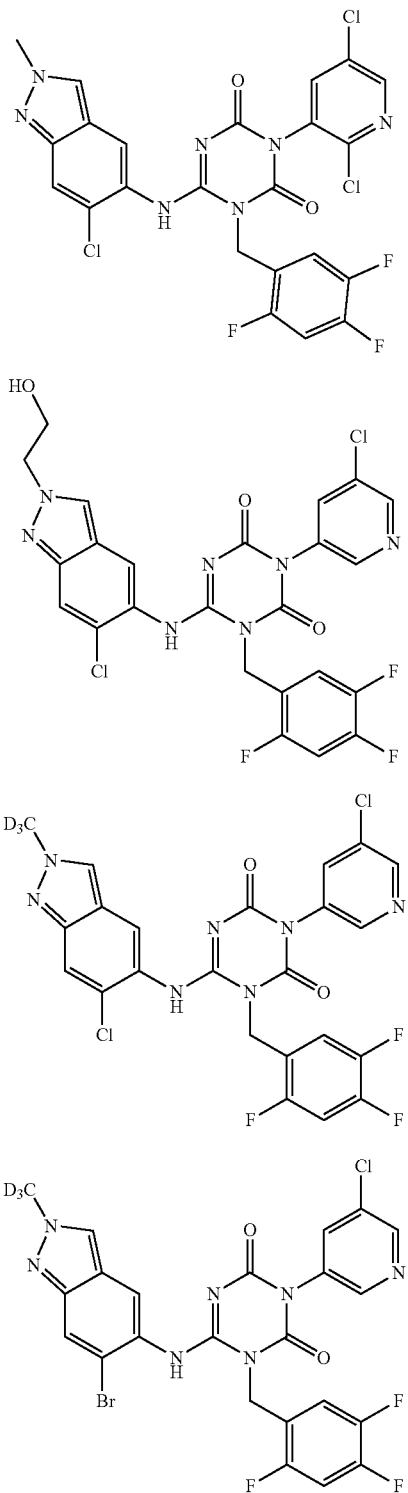

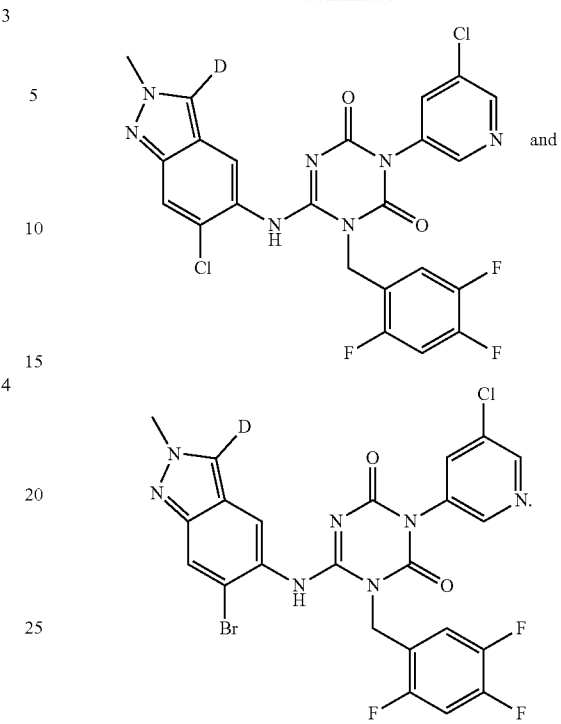

8. A pharmaceutical composition, comprising:
the compound of claim 1, or a pharmaceutically acceptable salt thereof, or a deuterium substitute thereof, or an isomer thereof, or a prodrug thereof; and
a pharmaceutically acceptable excipient.

9. A method for treating a virus infection in a subject, comprising administering to the subject an effective amount of the pharmaceutical composition of claim 8.

10. The method of claim 9, wherein the virus is selected from the group consisting of Middle East syndrome-associated coronavirus (MERS-COV), severe acute respiratory syndrome-associated coronavirus (SARS-COV), influenza A virus, influenza B virus, novel coronavirus (SARS-COV-2), Spanareh influenza virus, sandy virus, Bunyavirus, rabies virus, avian influenza virus, poliovirus, rhinovirus, adenovirus, Ebola virus, enterovirus, hepatitare A virus, hepatitare C virus, hepatitare E virus, enterovirus, HIV virus, echovirus, filovirus, measles virus, yellow fever virus, Japanese encephalitare virus, West Nile virus, Newcastle dareease virus, RS virus, vesicular stomatitare virus, mumps virus, dengue virus, coxsackie virus, rotavirus, and tobacco mosaic virus.

11. A method for inhibiting a coronavirus 3C-likeprotease (3CLpro), comprising
administering to the 3CLpro an effective amount of the compound of claim 1, or a pharmaceutically acceptable salt thereof, or a deuterium substitute thereof, or an isomer thereof, or a prodrug thereof.

* * * * *